(12) United States Patent
Vaz

(10) Patent No.: US 11,650,212 B2
(45) Date of Patent: May 16, 2023

(54) SCREENING METHOD FOR CEREBROTENDINOUS XANTHOMATOSIS USING BILE ALCOHOL GLUCURONIDES AND METABOLITE RATIOS

(71) Applicant: Academisch Medisch Centrum, Amsterdam (NL)

(72) Inventor: Frederic Maxime Vaz, Amsterdam (NL)

(73) Assignee: Academisch Medisch Centrum, Amsterdam (NL)

( * ) Notice: Subject to any disclaimer, the term of this patent is extended or adjusted under 35 U.S.C. 154(b) by 440 days.

(21) Appl. No.: 16/491,832

(22) PCT Filed: Mar. 4, 2018

(86) PCT No.: PCT/EP2018/055236
§ 371 (c)(1),
(2) Date: Sep. 6, 2019

(87) PCT Pub. No.: WO2018/162362
PCT Pub. Date: Sep. 13, 2018

(65) Prior Publication Data
US 2021/0033626 A1 Feb. 4, 2021

(30) Foreign Application Priority Data
Mar. 6, 2017 (EP) ..................................... 17159344

(51) Int. Cl.
*G01N 33/68* (2006.01)
(52) U.S. Cl.
CPC ..... *G01N 33/6893* (2013.01); *G01N 33/6848* (2013.01); *G01N 2333/90261* (2013.01); *G01N 2560/00* (2013.01); *G01N 2800/08* (2013.01)

(58) Field of Classification Search
CPC .......... G01N 33/6893; G01N 33/6848; G01N 2333/90261; G01N 2560/00; G01N 2800/08
See application file for complete search history.

(56) References Cited

U.S. PATENT DOCUMENTS

2004/0019027 A1* 1/2004 Forman .................. A61K 31/12
514/179

OTHER PUBLICATIONS

Haas et al. (Differential diagnosis in patients with suspected bile acid synthesis defects, World Journal of Gastroenterology, 2012, vol. 18, Issue 10, pp. 1067-1076) (Year: 2012).*
Pierre, Germaine, et al. "Prospective treatment of cerebrotendinous xanthomatosis with cholic acid therapy," J Inherit Metab Dis, (2008), vol. 31, Suppl. 2: S241-S245.
(Continued)

*Primary Examiner* — Elizabeth A Robinson
*Assistant Examiner* — Jean Caraballo-Leon
(74) *Attorney, Agent, or Firm* — McBee Moore & Vanik IP, LLC

(57) ABSTRACT

The invention relates to a method of diagnosing or screening for 27-hydroxylase (CYP27A1) deficiency in an animal comprising: determining in a biological sample the intensity signal by mass analysis of at least a bile alcohol glucuronide and a C24- or C27-bile acid or a conjugate thereof, comparing the intensity signals to a control sample or control value, and determining 27-hydroxylase (CYP27A1) deficiency based on said comparison.

11 Claims, 9 Drawing Sheets

(56) References Cited

OTHER PUBLICATIONS

Verrips, Aad, et al. "Clinical and molecular genetic characteristics of patients with cerebrotendinous xanthomatosis," Brain, (2000), vol. 123: 908-919.
Inoue, Kenji, et al. "Cholestanol Induces Apoptosis of Cerebellar Neuronal Cells," Biochemical and Biophysical Research Communications, (1999), vol. 256: 198-203.
Seyama, Yousuke. "Cholestanol Metabolism, Molecular Pathology, and Nutritional Implication," Journal of Medicinal Food, (2003), vol. 6, No. 3: 217-224.
Salen, Gerald, et al. "Chenodeoxycholic Acid Inhibits Increased Cholesterol and Cholestanol Synthesis in Patients with Cerebrotendinous Xanthomatosis," Biochemical Medicine, (1975), vol. 14: 57-74.
Berginer, Vladimir M., et al. "Long-Term Treatment of Cerebrotendinous Xanthomatosis with Chenodeoxycholic Acid," The New England Journal of Medicine, (1984), vol. 311, No. 26: 1649-1652.
Berginer, Vladimir M., et al. "Chronic Diarrhea and Juvenile Cataracts: Think Cerebrotendinous Xanthomatosis and Treat," Pediatrics, (2009), vol. 123, No. 1: 143-149.
Van Heijst, A.F.J., et al. "Treatment and follow-up of children with cerebrotendinous xanthomatosis," Eur J Pediatr, (1998), vol. 157: 313-316.
Yahalom, Gilad, et al. "Neurological Outcome in Cerebrotendinous Xanthomatosis Treated with Chenodeoxycholic Acid: Early Versus Late Diagnosis," Clinical Neuropharmacology, (2013), vol. 36, No. 3: 78-83.
Huidekoper, Hidde H., et al. "Hepatotoxicity due to chenodeoxycholic acid supplementation in an infant with cerebrotendinous xanthomatosis: implications for treatment," Eur J Pediatr, (2016), vol. 175: 143-146.
Appadurai, Vivek, et al. "Apparent underdiagnosis of Cerebrotendinous Xanthomatosis revealed by analysis of ~60,000 human exomes," Molecular Genetics and Metabolism, (2015), vol. 116: 298-304.
Lorincz, Matthew T., et al. "Cerebrotendinous Xanthomatosis," Arch Neurol, (2005), vol. 62: 1459-1463.
Bleyle, Lisa, et al. "Update on newborn dried bloodspot testing for cerebrotendinous xanthomatosis: An available high-throughput liquid-chromatography tandem mass spectrometry method," Molecular Genetics and Metabolism Reports, (2016), vol. 7: 11-15.
Debarber, Andrea E. et al. "A blood test for cerebrotendinous xanthomatosis with potential for disease detection in newborns," Journal of Lipid Research, (2014), vol. 55: 146-154.
Batta, Ashok K., et al. "Increased plasma bile alcohol glucuronides in patients with cerebrotendinous xanthomatosis: effect of chenodeoxycholic acid," Journal of Lipid Research, (1987), vol. 28: 1006-1012.
Ferdinandusse, Sacha, et al. "Peroxisomes and bile acid biosynthesis," Biochimica et Biophysica Acta, (2006), vol. 1763: 1427-1440.
Nakagawa, Michiko, et al. "Urinary bile alcohol profiles in healthy and cholestatic children," Clinica Chimica Acta, (2001), vol. 314: 101-106.
Mills, Kevin A., et al. "A Method for the Quantitation of Conjugated Bile Acids in Dried Blood Spots Using Electrospray Ionization-Mass Spectrometry," Pediatric Research, (1998), vol. 43: 361-368.
Dayal, Bishambar, et al. "Bile alcohol glucuronides: regioselective O-glucuronidation of 5beta-cholestane-3α,7α,12α,25tetrol and 24-nor-5beta-cholestane-3α,7α,12α,25-tetrol," Carbohydrate Research, (1993), vol. 240: 133-142.
Clayton, P.T., et al. "Mutations in the sterol 27-hydroxylase gene (CYP27A) cause hepatitis of infancy as well as cerebrotendinous xanthomatosis," J Inherit Metab Dis, (2002), vol. 25: 501-513.
Honda, Akira, et al. "Differences in hepatic levels of intermediates in bile acid biosynthesis between Cyp27-/- mice and CTX," Journal of Lipid Research, (2001), vol. 42: 291-300.
Hanson, Russell F., et al. "Metabolism of 5beta-cholestane-3α,7α,12α,26-tetrol and 5beta-cholestane-3α,7α,12α,25-tetrol into cholic acid in normal human subjects," Journal of Lipid Research, (1979), vol. 20: 489-493.
Dayal, B., et al. "Preparation of [3beta-3H] Labeled Bile Acids and Bile Alcohols," Steroids, (1979), vol. 34, No. 3: 259-271.
Vaz, Frederic M., et al. "A newborn screening method for cerebrotendinous xanthomatosis using bile alcohol glucuronides and metabolite ratios," Journal of Lipid Research, (2017), vol. 58: 1002-1007.
Salen, Gerald, et al. "Bile Alcohol Metabolism in Man: Conversion of 5beta-Cholestane-3α,7α,12α,25-tetrol to Cholic Acide," The Journal of Clinical Investigation, (1975), vol. 56: 226-231.
Kuriyama et al."Cerebrotendinous xanthomatosis: clinical and biochemical evaluation of eight patients and review of the literature," Journal of the Neurological Sciences, 102, 1991, pp. 225-232 (8 pages).
Pitt, "High-throughput urine screening for Smith-Lemli-Opitz syndrome and cerebrotendinous xanthomatosis using negative electrospray tandem mass spectrometry," Science Direct, Clinica Chimica Acta, 380, 2007, pp. 81-88 (8 pages).

\* cited by examiner

SCREENING METHOD FOR CEREBROTENDINOUS XANTHOMATOSIS USING BILE ALCOHOL GLUCURONIDES AND METABOLITE RATIOS

FIELD OF THE INVENTION

The teachings described herein relate to methods and kits directed to screening or diagnosing Cerebrotendinous xanthomatosis in blood samples.

BACKGROUND

Cerebrotendinous xanthomatosis (CTX) is a rare autosomal recessive disorder caused by the deficiency of 27-sterol hydroxylase (encoded by the CYP27A1 gene), which plays a crucial role in bile acid synthesis. CTX in adults is characterized by a progressive neurological phenotype. Symptoms during infancy and childhood include neonatal cholestasis, intractable diarrhoea (can be the presenting sign and clinically significant shortly after birth), bilateral cataract and developmental delay. From the second or third decade onward tendon xanthomas and neuropsychiatric symptoms, including pyramidal and cerebellar signs, peripheral neuropathy and dementia are observed (1, 2). The metabolic block in bile acid synthesis results in the deficiency of the primary bile acids cholic acid (CA) and particularly chenodeoxycholic acid (CDCA) in addition to the accumulation of 7α-hydroxy-4-cholesten-3-one. 7α-hydroxy-4-cholesten-3-one is further converted into different metabolites including cholestanol and characteristic bile alcohols. Cholestanol, together with cholesterol, accumulates in tissues. While the pathophysiology of CTX is still poorly understood, cholestanol is believed to cause the majority of the observed pathology. Cholestanol has been shown to induce apoptosis of neuronal cells and its accumulation is thought to underlie the observed neurodegeneration (3, 4). The development of symptoms and signs can be halted or prevented by supplementation of CDCA, which downregulates bile acid synthesis through a feedback mechanism that results in the inhibition of cholesterol-7α-hydroxylase, thereby preventing the production and accumulation of cholestanol (5). The prognosis of CTX is good when therapy is started early, but is less favourable when initiated at a later age (6-9). An early start of the therapy can prevent the neurological phenotype completely and patients are expected to remain symptom-free if treatment is started immediately after neonatal diagnosis (7, 10). Using allele frequencies of pathogenic CTX variants in the ExAC database, the incidence of CTX was estimated in different ethnic groups to be as high as 1:36,072 to 1:263,222 (11). This and other studies suggest that CTX may be underdiagnosed (11, 12). Taken together, this makes CTX an excellent candidate disease, especially for newborn screening. The detection of CTX newborn patients, however, is hampered by the absence of a suitable neonatal screening method in dried blood spots (DBS). DeBarber and coworkers have published a candidate, high-throughput, newborn screening method for CTX based on the quantification of a ketosterol intermediate in DBS using an LC-ESI/MS/MS method (13, 14). A potential disadvantage is that a derivatization-step is required before analysis, complicating implementation into existing neonatal screening programs, and at higher costs.

It is an objective of this invention to provide for a screening of diagnosis test which does not require a derivatization-step and is sensitive and specific enough to detect CTX in large screenings.

SUMMARY

This invention is based on the surprising finding that by determining the mass intensity signals of a bile alcohol glucuronide and a C24- or C27-bile acid or a conjugate thereof in a biological sample from a person, it is possible to accurately determine whether or not that person suffers from a 27-hydroxylase (CYP27A1) deficiency, using a method that does not require a derivatization-step. While it was known that bile alcohol glucuronides are elevated in plasma CTX patients (15), the levels of these metabolites vary between individuals. Moreover, the levels of these metabolites also deviate from normal levels in patients suffering from Zellweger syndrome and cholestasis patients. It was therefore unpredictable whether mass intensity signals would be informative to discriminate between CTX patients and normal controls or patients suffering from other diseases.

It was first investigated whether the measurement of the tetrol alone was sufficient to discriminate untreated newborn (and adult) CTX dried blood spots (DBS) from control newborn DBS. No stable isotope labeled internal standard is commercially available for the tetrol and several commercially available candidates were tested as internal standard, namely $^2H_4$-t-CDCA, $^2H_4$-g-CDCA, $^2H_4$-t-CA, $^2H_4$-g-CA and pregnanediol glucuronide (FIG. 2). Tetrol response was clearly elevated in most patients, but was not completely separated from the term/preterm controls. As previously reported, Zellweger patients and patients with cholestatic liver disease also have elevated levels of bile alcohols (16, 17) and in this experiment the Zellweger patients could not be distinguished from CTX by solely measuring the tetrol response, regardless of which internal standard was used (FIG. 2).

The determination of the concentration of four bile acids (t-CA, g-CA, t-CDCA, g-CDCA) and the taurine conjugate of the bile acid intermediate trihydroxycholestanoic acid (t-THCA) were added to the protocol in order to investigate whether a combination of bile alcohol glucuronide and a bile acid would enable discrimination of the CTX patients from the Zellweger patients and patients with other causes of cholestatic liver disease. FIG. 3 shows that these five metabolites could be measured in DBS using the corresponding stable isotope labeled internal standards. Bile acid and t-THCA concentrations in CTX patients were at the low end of the control range and t-THCA clearly accumulated in Zellweger patients. Other combinations with other primary bile acid conjugates are shown in FIG. 4. It was possible to discriminate CTX patients from controls, based on the ratio between the levels of bile alcohol glucuronide and C24- or C27-bile bile acid conjugates.

Therefore, the invention provides a method of diagnosing or screening for 27-hydroxylase (CYP27A1) deficiency comprising: a) determining in a biological sample the intensity signal by mass analysis of at least a bile alcohol glucuronide and a C24- or C27-bile acid or a conjugate thereof, b) comparing the ratio of said intensity signals to a control sample or control value, and c) determining 27-hydroxylase (CYP27A1) deficiency based on said comparison.

It was found that tetrol provides the best discriminative power when plasma, blood or serum is used. Therefore, in a preferred embodiment, said bile alcohol glucuronide comprises cholestanetetrol glucuronide (tetrol).

Preferably, said C24- or C27-bile acid or a conjugate thereof is selected from: cholic acid (CA), tauro-cholic acid (t-CA), glyco-cholic acid (g-CA), chenodeoxycholic acid (CDCA), tauro-chenodeoxycholic acid (t-CDCA), glyco-chenodeoxycholic acid (g-CDCA), trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA). The advantage is that these compounds provide a very good discriminative power in the method of the invention.

Preferably, at least the intensity is determined of a first and a second compound, wherein said first compound is selected from:

cholic acid (CA), tauro-cholic acid (t-CA), glyco-cholic acid (g-CA), chenodeoxycholic acid (CDCA), tauro-chenodeoxycholic acid (t-CDCA), and glyco-chenodeoxycholic acid (g-CDCA), and said second compound is selected from:

trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA). Using the mass intensity signals of said first and said second compound, at least a first ratio between the mass intensities of said bile alcohol glucuronide and the mass intensities of said first compound is determined and a second ratio between said second ratio between the mass intensities of said bile alcohol glucuronide and the mass intensities of said first compound is determined. An advantage of using at least two ratios is that this results in a lower number of false positives.

Most preferred bile acids are t-CDCA and t-THCA, as these have the most discriminative power when determined in combination with tetrol.

It was further found that the t-THCA/tetrol ratio has a high specificity of CTX detection with respect to Zellweger syndrome and cholestatic liver disease (see FIG. 1a). Indeed, the t-THCA/tetrol ratio separated all CTX cases from the three Zellweger syndrome cases and controls in our pilot study (Table 2A). Therefore, in a preferred embodiment, the method comprises determining the t-THCA/tetrol ratio.

It was further observed that in CTX, tetrol levels are high and t-CDCA levels are low, resulting in a markedly increased tetrol/t-CDCA ratio in CTX DBS, whereas this ratio is expected to be (almost) normal in patients with Zellweger syndrome or decreased in patients with cholestatic liver disease. This ratio showed excellent separation between all CTX DBS and the DBS of all controls (FIG. 1B), including those with hypercholanemia, and Zellweger patients. The control with the highest tetrol/t-CDCA ratio was 13.1 times lower than the lowest CTX tetrol/t-CDCA. This indicates that this ratio is an excellent candidate biomarker for the detection of CTX patients in DBS with newborn screening. Therefore, in another preferred embodiment, the method comprises determining the tetrol/t-CDCA ratio.

In a preferred embodiment said first and said second ratio comprise the tetrol/t-CDCA and the t-THCA/tetrol ratio. The t-CDCA/tetrol and the tetrol/t-THCA ratio are considered equivalent and are also encompassed.

An additional benefit of these ratios is that it is different in cholestatic liver disease, further enhancing specificity for CTX. FIG. 1 shows the rationale of the two ratios (FIG. 1A) as well as the results of the metabolite ratios for term (n=150) and preterm (n=50) controls, Zellweger (n=3) and CTX patients (n=14) (FIG. 1B and Table 2(A)).

With the tetrol/t-CDCA ratio 100% separation was achieved between the CTX patients, both with dried blood spots (DBS) from newborns and from older patients, and control (term/preterm) subjects and Zellweger patients. The t-THCA/tetrol ratio could distinguish CTX DBS from the Zellweger syndrome DBS and control DBS. In addition, hypercholanemic controls could be accurately separated from the CTX patients using both the tetrol/t-CDCA ratio (hypercholanemic range: 0.000-0.018) and the t-THCA/tetrol ratio (hypercholanemic range: 2.5-311), thus enhancing the specificity for CTX by excluding subjects with hypercholanemia.

A DBS of a CTX patient (P9) with a tetrol/t-CDCA ratio in the low end of the spectrum was used to investigate the precision of the metabolite ratio(s) of the method of the invention. For a DBS assay, the interassay precision of the tetrol/t-CDCA ratio was acceptable at 14% (0.64±0.09, n=10). The interassay precision of the t-THCA/tetrol was higher (63%) due to low t-THCA concentration in the CTX sample resulting in low t-THCA/tetrol values (0.07±0.04, n=10), but this variation was small compared to the difference between control and CTX DBS and is therefore not expected to influence the specificity of the method for CTX. Therefore, in a preferred embodiment, the method comprises determining the ratio between the intensities of tetrol and t-THCA in dried blood spot samples, as determined using mass analysis.

Preferably, said mass analysis comprises MS, LC-ESI, flow-injection MS.

In another preferred embodiment, the intensity is determined of a stable isotope labeled compound selected from: tetrol, bile alcohol glucuronide, a C24- or C27-bile acid or a conjugate thereof, and wherein said intensity of said stable isotope is compared to said intensity signal by of said bile alcohol glucuronide and said C24- or C27-bile acid or a conjugate thereof. An advantage is that a stable isotope may be used to accurately quantify the concentrations of said bile alcohol glucuronide and a C24- or C27-bile acid or a conjugate thereof.

The invention further provides a kit for diagnosing or screening for 27-hydroxylase (CYP27A1) deficiency comprising a stable isotope labeled tetrol and a stable isotope labeled C24- or C27-bile acid or a conjugate thereof selected from the group consisting of cholic acid (CA), tauro-cholic acid (t-CA), glyco-cholic acid (g-CA), chenodeoxycholic acid (CDCA), tauro-chenodeoxycholic acid (t-CDCA), glyco-chenodeoxycholic acid (g-CDCA), trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA).

Preferably, said kit further comprises a positive control sample, preferably a blood sample of a CTX patient.

DETAILED DESCRIPTION

Definitions

Figure 1:
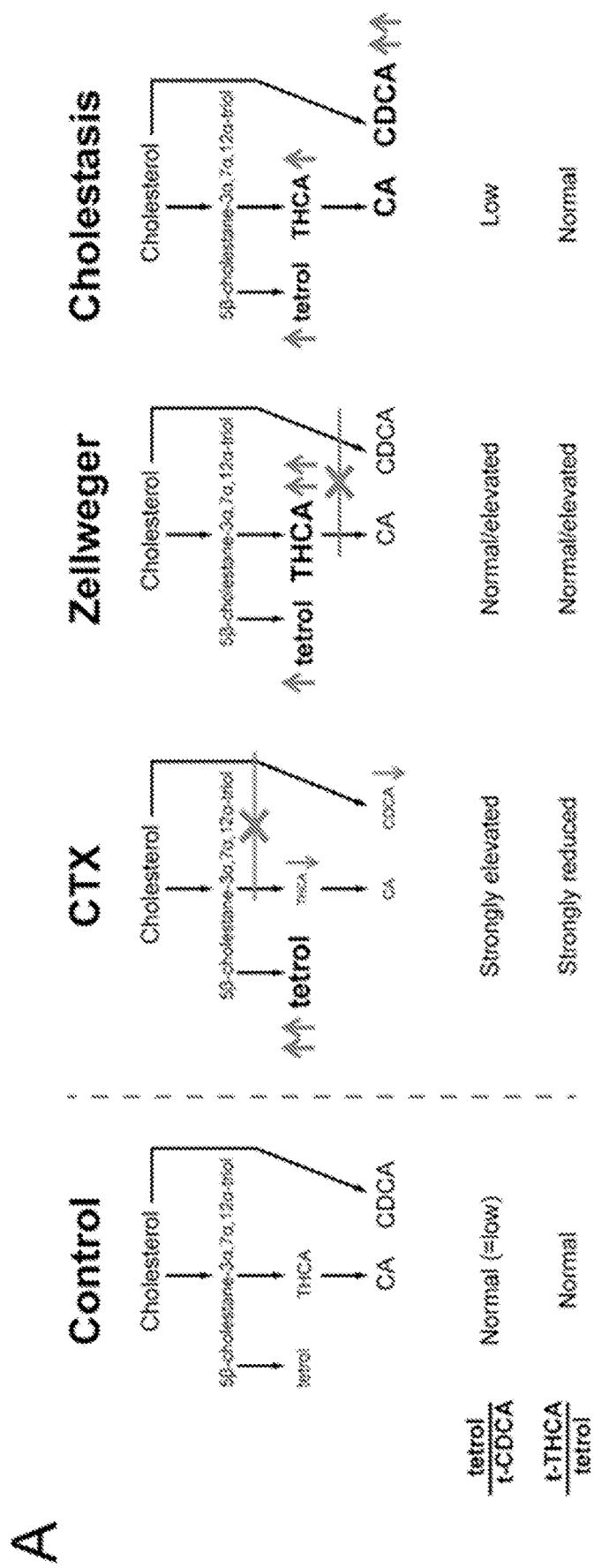
FIG. 1 shows that ratios enhance selectivity and specificity of the CTX screening assay. (A) Rationale of the two selected ratios. Tetrol/t-CDCA ratio: In CTX tetrol accumulates and CDCA is deficient yielding a strongly elevated ratio. In Zellweger tetrol is elevated but CDCA is normal resulting in a normal or slightly elevated ratio, while during cholestasis CDCA (and CA) is elevated keeping the ratio low. t-THCA/tetrol ratio: In CTX this ratio is strongly reduced, while normal or elevated in Zellweger and cholestasis. (B) Tetrol/t-CDCA and t-THCA/tetrol ratios in term/preterm controls (triangle), Zellweger (diamond), newborn CTX and untreated CTX patients (open/closed circle). The tetrol/t-CDCA ratio is highly discriminative, also for Zellweger and CTX. The t-THCA/tetrol ratio also discriminates Zellweger and CTX.
Figure 1:
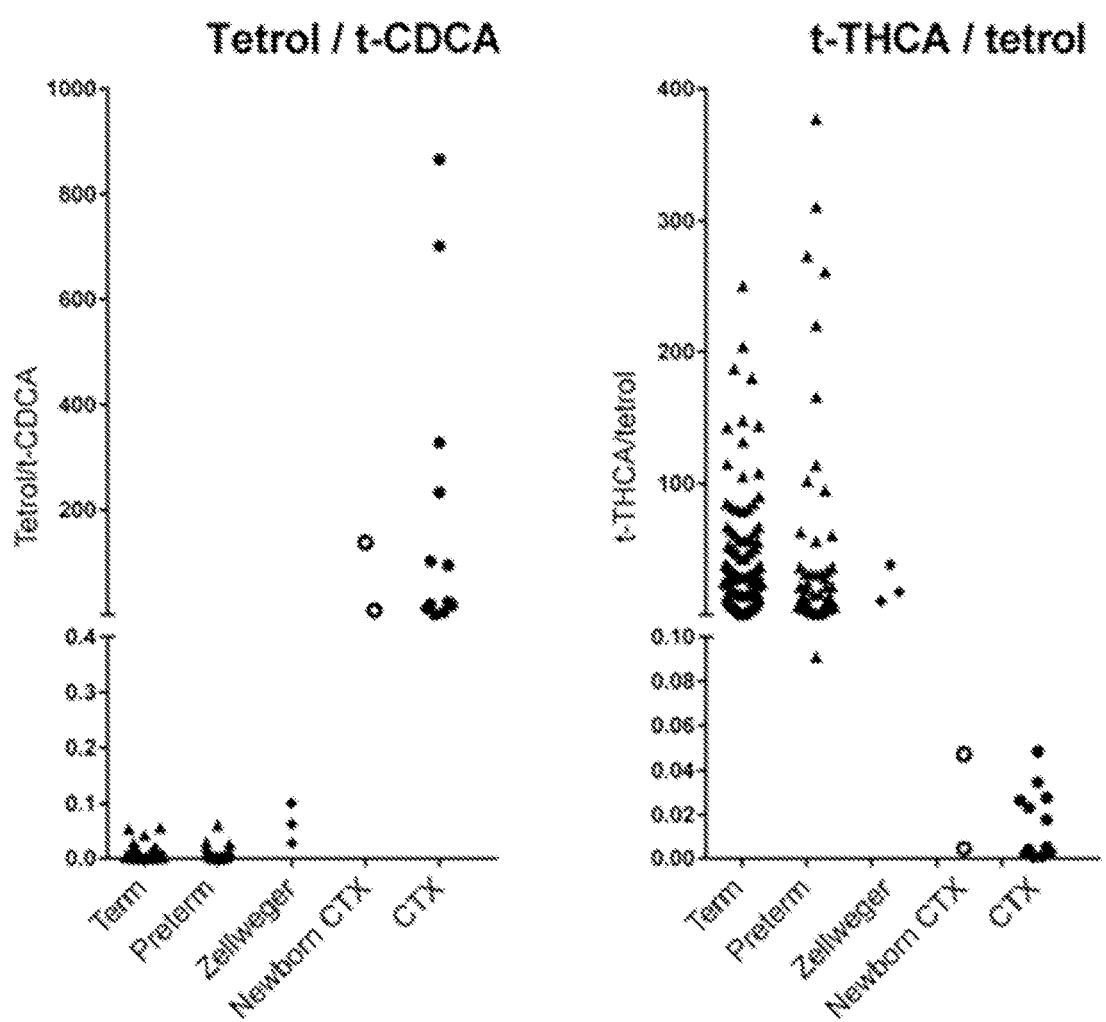

As used herein, the terms "diagnosis" "diagnose" and "diagnosing" refer to the process of attempting to determine or identify whether or not a subject is suffering from a given disease or condition. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject. Diagnosis as used herein also includes methods for preliminary diagnosis which could be confirmed by diagnosis using other methods known in the art. Additionally, it is contemplated that the methods as described herein may be used for monitoring the progression of a condition and/or the efficacy of a therapy being used to treat a condition.

The term "bile acid," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocholate, and the like.

The term "primary" bile acid refers to any of cholic acid (3α,7α,12α-trihydroxy-5β-cholanoic acid) and chenodeoxycholic acid (3α,7α-dihydroxy-5β-cholanoic acid).

The term "secondary bile acid" as used herein refers to any of primary bile acid and conjugate thereof that has been modified by bacteria in the gut, including but not limited to lithocholic acid and deoxycholic acid.

The term "C24 bile acid" as used herein refers to any primary and secondary bile acid and conjugates thereof having 24 carbon atoms.

The term "C27 bile acid" as used herein refers to any bile acid intermediate and conjugate thereof having 27 carbon atoms, which can be formed in the bile acid synthesis before and during peroxisomal beta-oxidation.

The term "conjugate of a bile acid" refers to any primary bile acid conjugated to the amino acids glycine and taurine.

The term "bile acid intermediate" refers to any metabolite between cholesterol and the primary bile acids that are formed by normal or pathological bile acid metabolism/synthesis.

As used herein the term "bile alcohol glucuronide" refers to a conjugate of a bile alcohol with glucuronic acid.

The term "tetrol" as used herein refers to 5β-cholestane-3α,7α,12α,25-tetrol glucuronide and the isomers of cholestanetetrol glucuronide. Preferably, tetrol is 5β-cholestane-3α,7α,12α,25-tetrol glucuronide.

The term "control sample" as used herein refers to a biological sample or samples of a patient suffering from CTX, or another positive or negative control sample for determining control intensity signals.

The term "control value" as used herein refers to a predetermined intensity signal or ratio for said at least a bile alcohol glucuronide and a C27- or C24-bile acid bile acid or a conjugate thereof and/or a predetermined cut-off level.

Preferably, a control value refers to control level of said bile alcohol glucuronide and a C27- or C24-bile acid bile acid or a conjugate thereof and/or a predetermined intensity signal level or ratio of the intensity signals between said at least a bile alcohol glucuronide and a C27- or C24-bile acid bile acid or a conjugate thereof and/or a predetermined cut-off level. The control value can for example be a reference intensity signal to which test sample intensity signals are compared, and/or a predetermined intensity signal or signals for example as a numerical value and/or range (e.g. control range) corresponding to the intensity signal levels in such sample or samples. For example, as demonstrated herein, control samples with a known outcome (such as suffering from CYP27A1 deficiency, Zellweger, cholestasis or from a healthy control) can be used to determine a cut-off above or below which subjects are predicted to suffer from CYP27A1 deficiency. Test samples are then compared to the predetermined value determined using control samples. The control value can be an average, median, or calculated cut-off intensity value (e.g. threshold) for said bile alcohol glucuronide and a C27- or C24-bile acid bile acid or a conjugate thereof and/or a composite thereof (e.g. ratio, sum) above or below which value a subject can be classified with an outcome class—e.g. CYP27A1 deficiency or not.

In an embodiment, the control can be a ratio of the intensities of said bile alcohol glucuronide and a C27- or C24-bile acid bile acid or a conjugate thereof and the mass intensity of one or more internal standardization markers in a control sample. The control ratio is compared to a corresponding ratio determined for the sample.

The term "ratio" as used herein refers to the mathematical relationship between two quantities. For instance, a ratio of quantities A and B is a quotient of value A divided by value B or of value B by A. As used herein, the ratios A/B and B/A can be used interchangeably. Therefore, if it is stated herein that the ratio between the mass intensities of C24- or C27-bile acid or a conjugate thereof is determined, said ratio comprises the mass intensity of said C24-bile acid divided by the mass intensity of said C27-bile acid and the mass intensity of said C27-bile acid divided by the mass intensity of said C24-bile acid.

EMBODIMENTS

Figure 2:
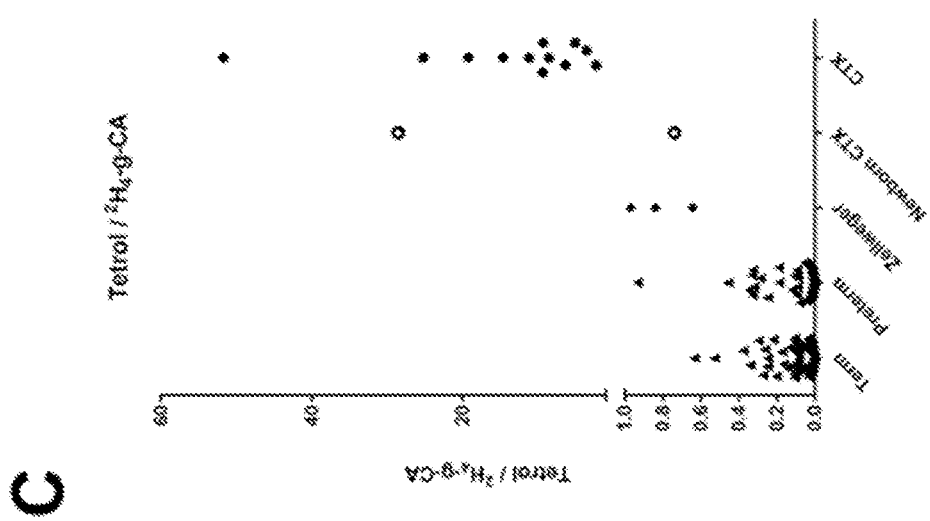
FIG. 2 shows the tetrol response in term/preterm controls (triangle), Zellweger (diamond), newborn CTX and untreated CTX patients (open/closed circle) calculated using different internal standards, (A) pregnanediol glucuronide (B)$^2$H$_4$-t-CA (C)$^2$H$_4$-g-CA (D)$^2$H$_4$-t-CDCA and (E) $^2$H$_4$-g-CDCA. Despite a clear elevation of the tetrol response for all used internal standards, the separation of controls and CTX patients was not satisfactory. Zellwegers showed a considerably increased tetrol response which overlapped with the CTX range.
Figure 2:
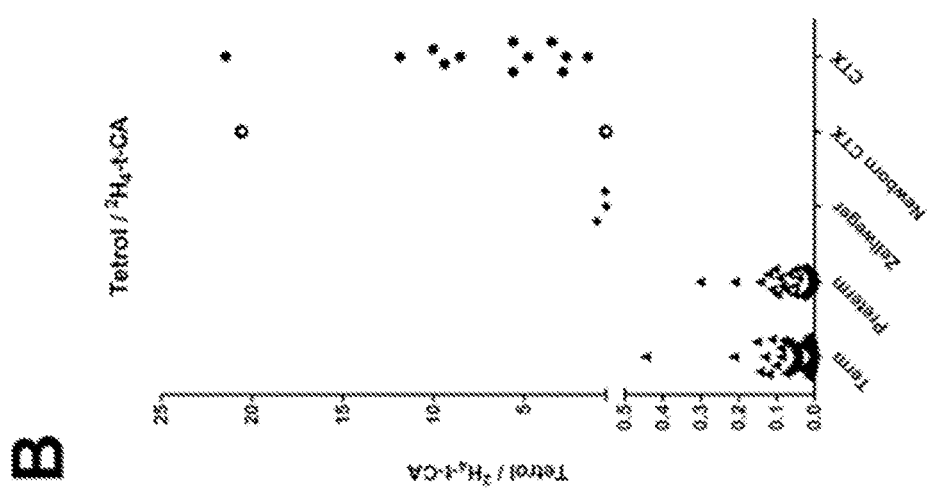
Figure 2:
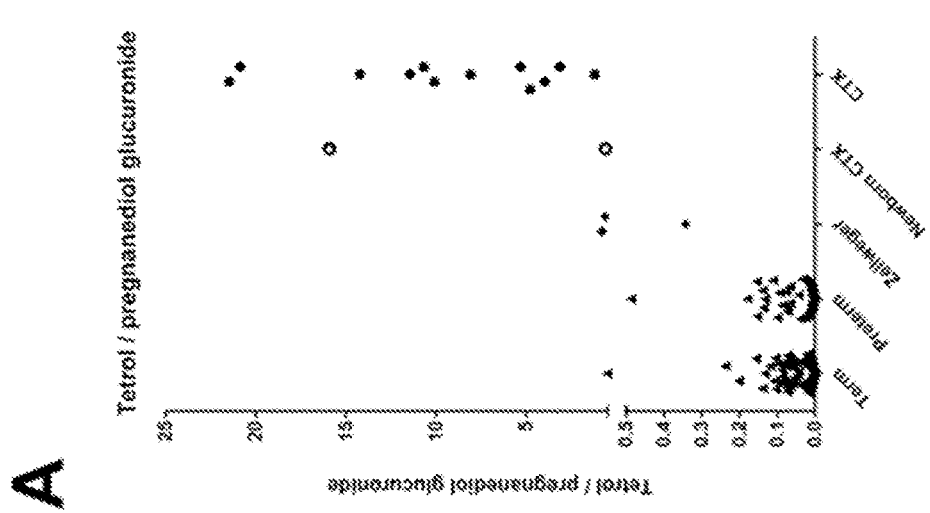
Figure 2:
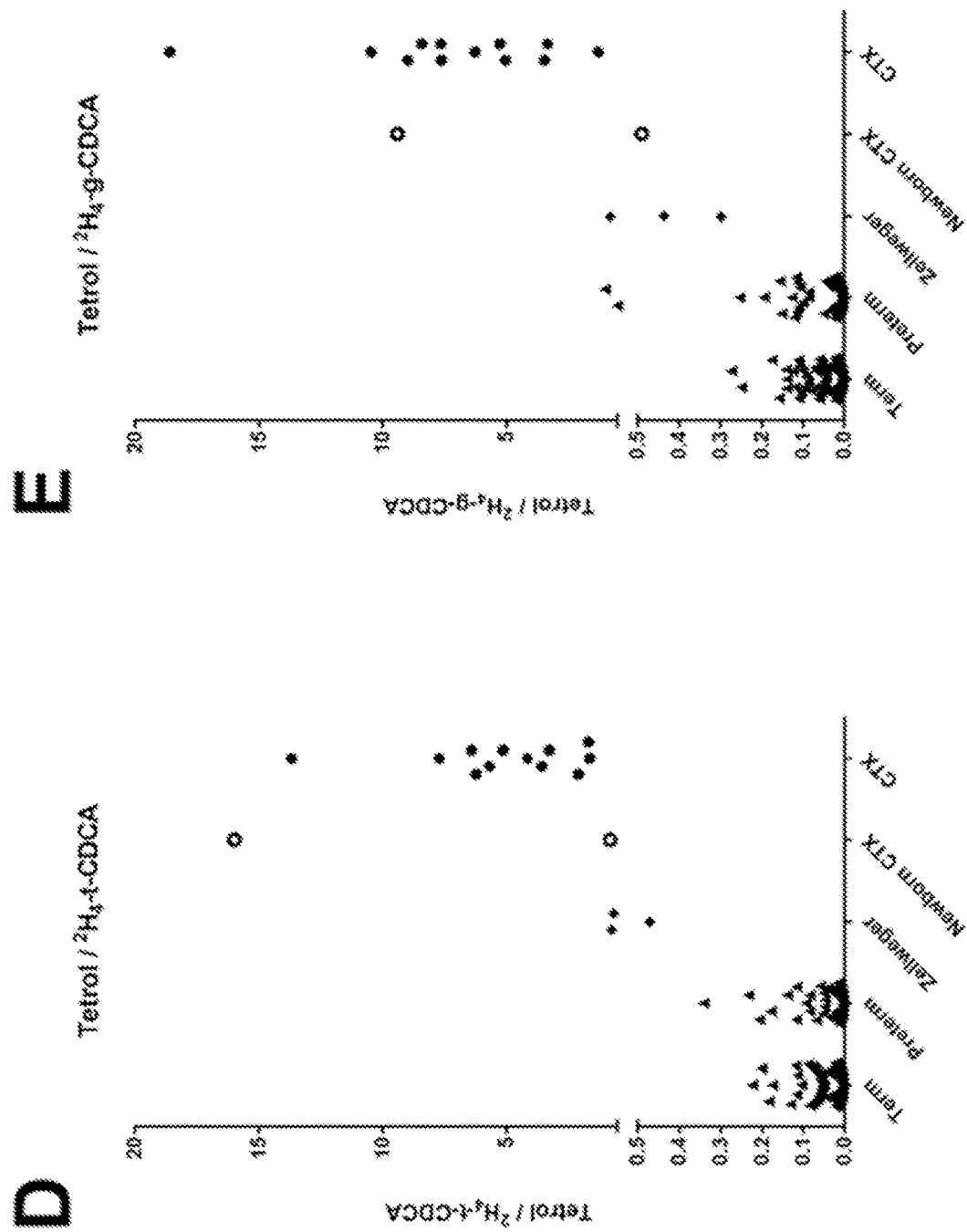
Figure 3:
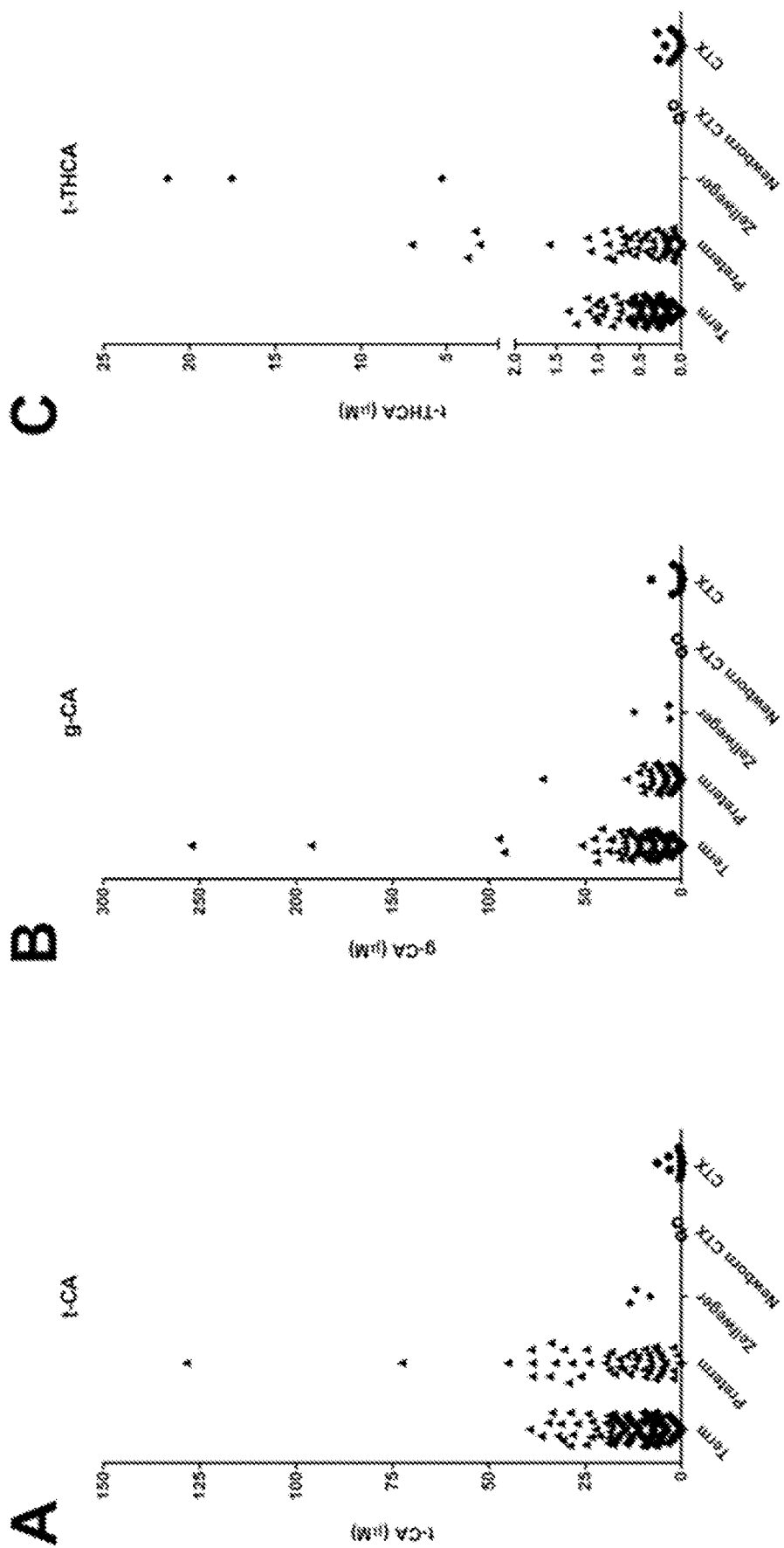
FIG. 3 shows the concentrations of bile acid and the bile acid intermediate t-THCA in term/preterm controls (triangle), Zellweger (diamond), newborn CTX and untreated CTX patients (open/closed circle) calculated different internal standards, (A) t-CA, (B) g-CA, (C) t-THCA, (D) t-CDCA and (E) g-CDCA. Bile acid and t-THCA concentrations in CTX patients were at the low end of the control range. As expected, t-THCA clearly accumulated in Zellweger patients.
Figure 3:
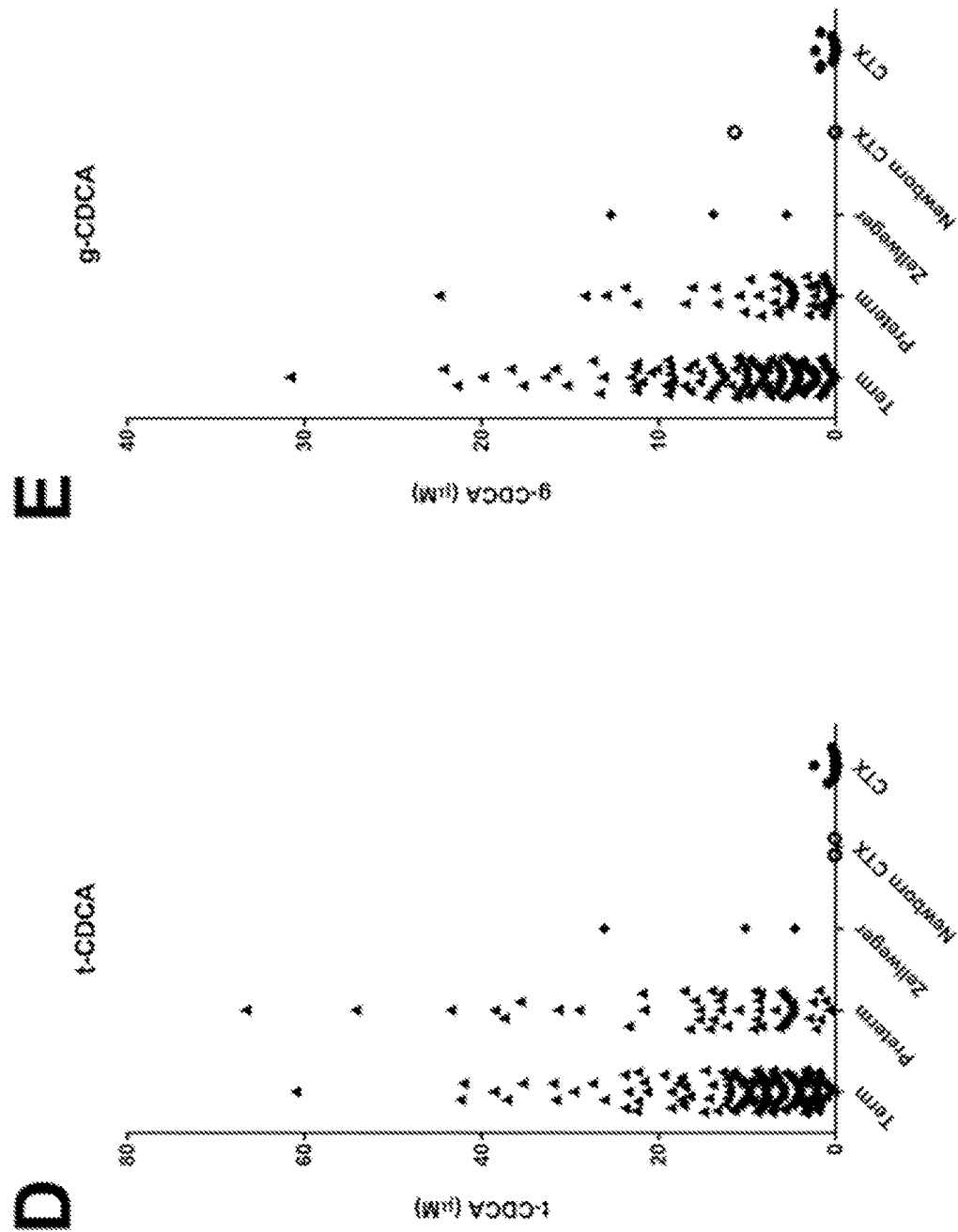
Figure 4:
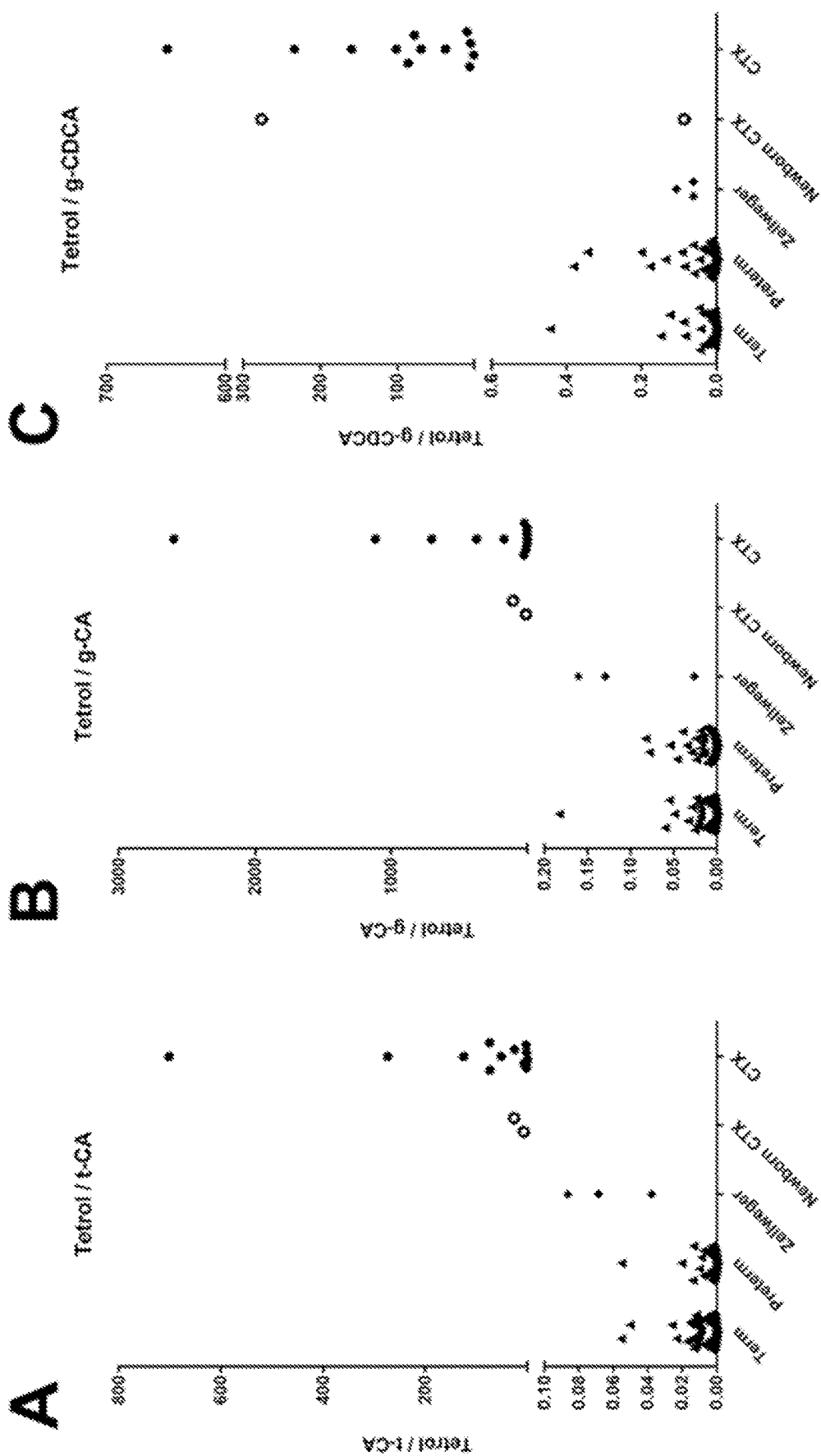
FIG. 4 shows other investigated metabolite ratios in term/preterm controls (triangle), Zellweger (diamond), newborn CTX and untreated CTX patients (open/closed circle): (A) tetrol/t-CA, (B) tetrol/g-CA and (C) tetrol/g-CDCA. The tetrol/t-CDCA ratio provided the best discriminative power.
Figure 5:
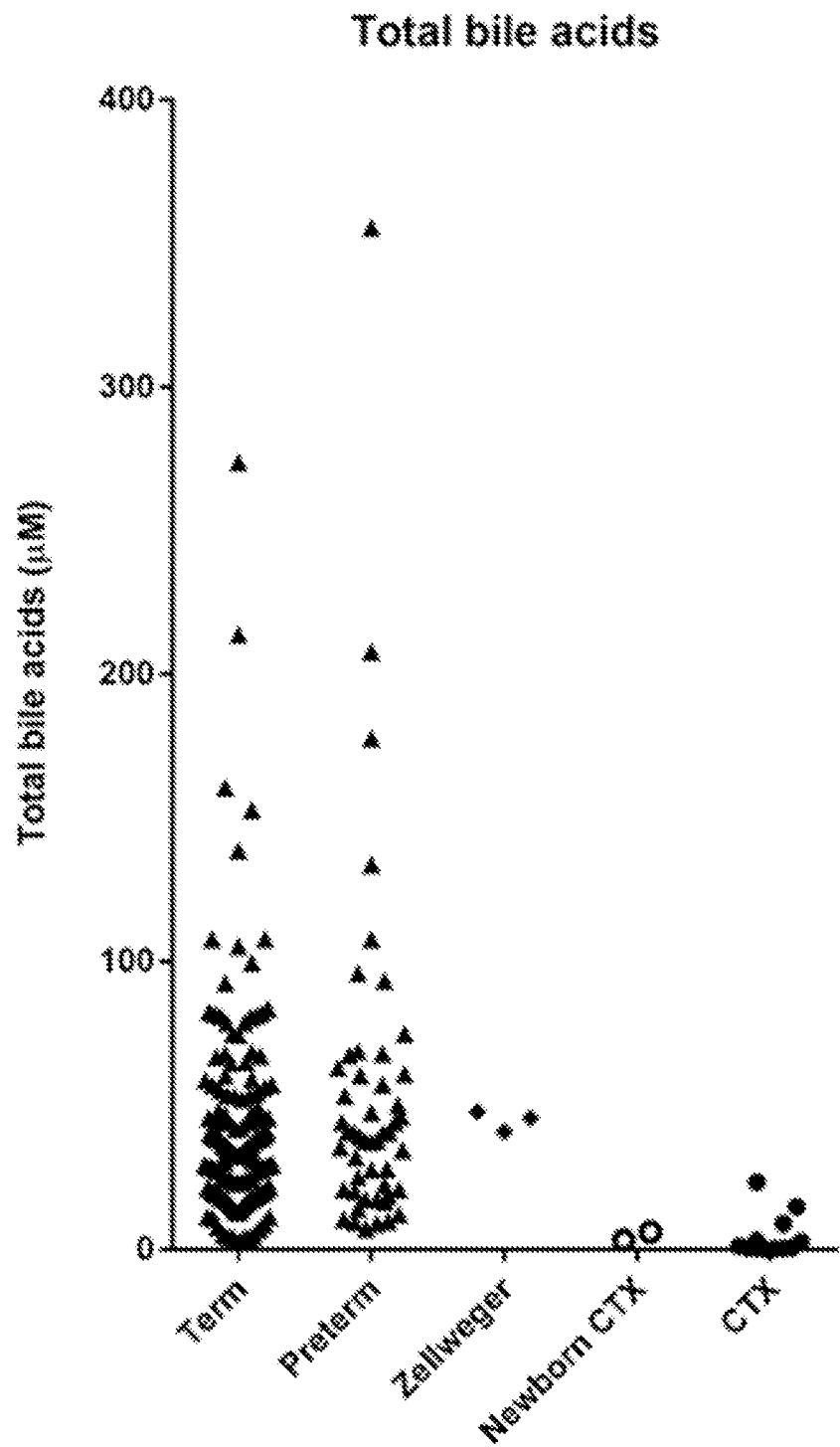
FIG. 5 shows the total bile acid levels in term/preterm controls (triangle), Zellweger (diamond), newborn CTX and untreated CTX patients (open/closed circle).

Based on the mass intensity signals of the accumulating cholestanetetrol glucuronide (tetrol) and specific bile acids/bile acid intermediates, we developed a new DBS screening assay for CTX that is suitable for neonatal screening. Using our assay, a good separation was achieved between DBS of CTX patients and DBS of controls, Zellweger patients and newborns with (potential) cholestasis. Initially, we set out to solely measure tetrol in untreated CTX patients. However, despite a fairly good separation between the mean response in controls and CTX patients, there was overlap between the responses for the patient and control groups (see FIG. 2). In addition, other disorders like Zellweger syndrome (16) and cholestatic liver disease (17) also lead to accumulation of tetrol or similar isobaric sterol alcohol glucuronides, as was also corroborated for the three Zellweger syndrome DBS in this study, for which tetrol levels were elevated. Thus, as it lacks sensitivity and is not specific enough to detect only CTX patients, quantification of tetrol alone is unsuitable as a neonatal screening test for CTX.

We found that a combination of mass measurements of bile alcohol glucuronide and a C24- or C27-bile acid or a conjugate thereof, resulted in a good sensitivity and specificity.

The invention therefore provides a method of diagnosing or screening for 27-hydroxylase (CYP27A1) deficiency in an animal comprising:
  a) determining in a biological sample the intensity signal by mass analysis of at least a bile alcohol glucuronide and a C27- or C24-bile acid or a conjugate thereof,
  b) determining the ratio between said bile alcohol glucuronide and said C24- or C27-bile acid or a conjugate thereof,
  c) comparing said ratio with the ratio of a control sample or control value,
  d) determining 27-hydroxylase (CYP27A1) deficiency based on said comparison.

The method is suitable for diagnosis or screening of animals, in particular of mammals, and preferably it is used for humans. Preferred embodiments as described herein include diagnosing or screening methods for newborn screens. However, the methods as described herein are equally useful for other populations and screening/diagnosis such as toddlers, and adults.

The present teachings can provide methods for determining the relative concentration of the analytes selected from bile alcohol glucuronides and C24- or C27-bile acids or a conjugate thereof, in one or more samples and provide methods whereby the relative or absolute concentration, can be determined using mass spectrometry.

Preferably, ratios between the mass intensities of bile alcohol glucuronides and C24- or C27-bile acids and conjugates thereof, more preferably between the mass intensities of bile acid t-CDCA and tetrol, and the bile acid intermediate t-THCA and tetrol are used. Alternatively a look up table of the results can be searched and used as input for a formula that includes other parameters, for example plasma cholestanol or a scoring system of clinical readouts.

Any biological sample which comprises bile acid synthesis metabolites may be used in the method of the invention. For example, urine, and other bodily fluids are suitable. It is preferred that said biological sample is a blood, serum, or plasma. In particular, dried blood spots (DBS) are preferably used, as these samples are routinely used in newborn screening assays.

A very suitable biological sample comprises a quarter-inch (6.4 mm) diameter DBS punch (or for most CTX DBS; two eighth-inch DBS, which equals half the material in one quarter-inch DBS) whereas most neonatal screening laboratories prefer a one eighth-inch (3.2 mm) diameter DBS punch. A modern triple quadrupole tandem mass spectrometers will readily detect the three metabolites used in our assay in eighth-inch DBS punched. Conversely, our invention also shows that laboratories that have older machines still can screen for CTX with our method when using a quarter-inch diameter DBS punch (or two eighth-inch DBS).

In a preferred embodiment, said biological sample is a DBS not bigger than ¼ inch, ⅛ inch.

The biological sample can be subjected to chromatographic separation, for example, by LC such as by HPLC, followed by mass analysis.

The method can also comprise the step of extracting the analyte using either liquid-liquid extraction, solid-liquid-extraction or protein precipitation using hydrophobic solvents such as methanol prior to the mass analysis step.

In some preferred embodiments the mass spectrometer can be used in tandem MS mode with multiple-reaction monitoring (MRM) to detect the transitions of the analytes preferably, but not restricted to the bile alcohol glucuronides and C24- or C27-bile acids or a conjugate thereof listed in table 2. In these embodiments and in other preferred embodiments, a stable isotope labeled internal standard corresponding to the unlabeled ion to be detected is preferably used to calculate the concentration or abundance of these metabolites.

In some preferred embodiments, a mass spectrometer is used with high resolution capacities enabling the measurement of the exact mass in full scan mode to directly determine the abundance of the required ions with exact mass precision. During the analysis, the exact mass trace of ions listed in, but not restricted to those in, table 3 can be used for detection of bile acid metabolites. In these embodiments and in other preferred embodiments, a stable isotope labeled internal standard corresponding to the unlabeled ion to be detected is preferably used to calculate the concentration or abundance of these metabolites.

In a preferred embodiment, the abundance of each transition (or in case of a mass spectrometer with high-resolution capacity, the exact mass trace) during the elution/infusion of the sample can be averaged followed by correction for background signal by subtracting the average intensity prior or after the sample elution/infusion. This yields the intensity/abundance of the chosen analytes.

The intensity/abundance of the analytes can then be used to calculate the metabolite ratios. In these embodiments and in other preferred embodiments, if dedicated (stable-isotope labeled) internal standards are used, the internal standard can be used to correct for matrix effects, after which the resulting response can be used to perform metabolite calculations.

In preferred embodiments, the collision fragment energy is selected to be in the range of 35-60 eV.

In a preferred embodiment, flow injection mass analysis (HA) is used. An advantage thereof is that HA equipment belongs to standard newborn screening equipment.

Quantitation can be enabled by relative or absolute measurement of the signal derived from one or more analytes and standards. The negative charge can be transferred to the analyte which functions as the fragment ion to be detected by mass spectrometry.

In a preferred embodiment, an internal standard solution is added to the sample comprising the analytes. Preferably, said solution comprises one or more of pregnanediol glucuronide, stable isotope-($^{13}$C, $^2$H, etc.)-labeled tetrol-glucuronide, $^2$H$_4$-t-CDCA, $^2$H$_4$-g-CA, $^2$H$_4$-g-CDCA, preferably dissolved in methanol.

In some preferred embodiments, the "Parent-daughter ion transition monitoring" or "PDITM" is used as the method of analysis and workflow status. PDITM refers to a technique whereby the transmitted mass-to-charge (m/z) range of a first mass separator (often referred to as "MS" or the first dimension of mass spectrometry) is specifically selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as "MS/MS" or the second dimension of mass spectrometry) is selected to transmit one or more daughter ions to a detector which measures the daughter ion signal. This technique offers unique advantages when the detection of daughter ions in the spectrum is focused by "parking" the detector on the expected daughter ion mass. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal". For the parent ion-daughter combinations used in the method described herein, see Table 2.

In one embodiment of parent-daughter ion transition monitoring is multiple reaction monitoring (MRM) (also referred to as selective reaction monitoring). In various embodiments of MRM, the monitoring of a given parent-daughter ion transition comprises using the first mass separator (e.g., a first quadrupole parked on the parent ion m z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

In some preferred embodiments, a tandem mass spectrometer (MS/MS) instrument or, more generally, a multidimensional mass spectrometer instrument, can be used to perform PDITM, e.g., MRM. Examples of suitable mass analyzer systems comprise, but are not limited to, those that comprise one or more of a triple quadrupole, a quadrupole-linear ion trap, a quadrupole TOF, and a TOF-TOF, ion trap, orbitrap, quadrupole ion trap, quadrupole orbitrap.

In an embodiment a step of subjecting at least a portion of the combined sample to PDITM is applied, which comprises introducing the combined sample directly into a mass analyzer system, e.g., by introduction of the combined sample in a suitable solution using an electrospray ionization (ESI) ion source or atmospheric pressure ionization (APCI) source.

According to various preferred embodiments, samples containing one or more compounds may be enriched by various methods prior to analysis. The enrichment method can depend upon the type of sample, such as blood (fresh or dried), plasma, serum, etc. Exemplary enrichment methods can comprise, without limitation, protein precipitation, liquid-liquid extraction, solid-liquid extraction, and ultrafiltration. Other enrichment methods, or a combination of two or more enrichment methods may be used.

The sample workup of our method is straightforward as no derivatization is required and since a standard methanol extraction is used, the assay can suitably be combined with other neonatal screening assays. Therefore, in a preferred embodiment, said method is combined with other neonatal screening assays. The measurement uses preferably flow injection, as it only takes a few minutes per run.

Preferably, the method comprises the step of measuring specific transitions for cholestanetetrol glucuronide, taurochenodeoxycholic acid (t-CDCA) and tauro-trihydroxycholestanoic acid (t-THCA).

The invention further provides a kit for diagnosing or screening for 27-hydroxylase (CYP27A1) deficiency comprising a stable isotope labeled tetrol and a stable isotope labeled C24- or C27-bile acid or a conjugate thereof selected from the group consisting of cholic acid (CA), tauro-cholic acid (t-CA), glyco-cholic acid (g-CA), chenodeoxycholic acid (CDCA), tauro-chenodeoxycholic acid (t-CDCA), glyco-chenodeoxycholic acid (g-CDCA), trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA). A skilled person in the art knows how to synthesize stable isotope labelled bile acid. Methods to synthesize tetrol are known in the art (19).

Preferably, the kit further comprises a positive control sample, preferably a blood sample of a CTX patient.

In a further aspect, persons diagnosed with 27-hydroxylase (CYP27A1) deficiency, preferably in the newborn period, using the method of the invention, can be effectively treated with chenodeoxycholic acid (CDCA) supplementation administered orally, thereby preventing the development of any symptoms associated with cerebrotendinous xanthomatosis (CTX; 27-hydroxylase (CYP27A1) deficiency). In a preferred embodiment, CDCA supplementation comprises 5 mg/kg/day divided in three equal dosages. In another preferred embodiment, CDCA supplementation comprises 15 mg/kg/day in three equal dosages. This regime is preferred for children. In another preferred embodiment, CDCA supplementation comprises up to 250 mg three times daily. This regime is preferred for adult patients.

While the above description provides examples and specific details of various embodiments, it will be appreciated that some features and/or functions of the described embodiments admit to modification without departing from the scope of the described embodiments. The above description is intended to be illustrative of the teachings herein, the scope of which is limited only by the language of the claims appended hereto.

Example

Patient and Control Samples

Anonymized DBS of 150 term (mean gestational age (range): 39.9 (37.0-42.0) weeks and 50 preterm newborns (mean gestational age (range): 34.5 (26.7-36.9) weeks) were obtained from the biobank of the Dutch newborn screening program (Dutch National Institute for Public Health and the Environment, Bilthoven, The Netherlands). All parents gave informed consent for the anonymized use of DBS from the Guthrie card of their child at the time of collection (standard procedure in the Dutch newborn screening program; all Guthrie newborn screening cards in the Netherlands are stored for five years after which they are destroyed). Fifteen DBS, including 2 original neonatal DBS, were collected from 14 individual untreated CTX patients. These included DBS from participants enrolled in Institutional Review Board approved studies at Oregon Health & Science University with written informed consent provided by the participants for use of the DBS. De-identified diagnostic samples submitted to the Sterol Laboratory for biochemical confirmation of CTX were also used with Institutional Review Board approval. Table 1 lists all relevant details concerning the CTX patients and their DBS. All patients or their parents/legal representatives gave written informed consent for the use of their DBS/the DBS of their child. Three anonymized Zellweger DBS were obtained from the biobank at the Academic Medical Center (Amsterdam).

Materials

Solvents: methanol and acetonitrile were purchased from Biosolve. $^2H_4$-g-CDCA, $^2H_4$-g-CA, $^2H_4$-t-CDCA and $^2H_4$-t-CA were purchased from CDN Isotopes. $H_2O$ was MilliQ® purified water. 5β-Pregnane-3α,20α-diol glucuronide (Pregnanediol glucuronide) was from Sigma-Aldrich and filter paper Whatman 903 was purchased from Drukkerij PAL.

Sample Preparation

A punch (quarter-inch (6.4 mm) diameter) of a DBS was used for all except for CTX DBS number 1 to 8, 12 and 13, where two 3.2 mm DBS were used (for these, the result was corrected by multiplying the result by a factor two). The DBS were transferred to a 1.5 ml tube, to which 500 µL methanol was added and this was incubated for 30 min at room temperature in a sonicator bath (Branson 3510). The filter paper was removed, and the extraction fluid was transferred to a 4-mL glass tube followed by the addition of 20 µL internal standard mixture [1 µM Pregnanediol glucuronide, 0.25 µM $^2H_4$-t-CA, 0.25 µM $^2H_4$-t-CDCA, 0.25 µM $^2H_4$-g-CA, 0.25 µM $^2H_4$-g-CDCA dissolved in methanol/$H_2O$ (3:1 vol/vol)]. The internal standard solution was intentionally not added during the sonication step as this solution contains water which extracts unwanted salts/interfering compounds that interfere with the MS measurement. After vortex-mixing, the sample was taken to dryness under nitrogen flow at 40° C. The residue was reconstituted in 120 µL of methanol/$H_2O$ (3:1 vol/vol), transferred to a sample vial, and capped.

Flow Injection Ms/Ms

We injected 10 µL using Acetonitrile/$H_2O$ (9:1, vol/vol) as mobile phase into a Waters Premier-XE tandem mass spectrometer (MS/MS) (Waters Cooperation) operated in the negative ion electrospray ionization mode. Nitrogen was used as both the nebulizing and the desolvation gas. The collision gas was argon, and the cell pressure was $2.7*10^{-3}$ mbar. The source temperature was set at 120° C., and the capillary voltage was maintained at 2.5 kV. The detector was used in tandem MS mode with multiple-reaction monitoring to detect the transition of a specific precursor ion to a fragment for each analyte. The transitions, cone voltages, and collision energies established for each compound are listed in Table 2. The analytical run time, from injection to injection, was 2 minutes. Quantification was performed using Masslynx 4.2 employing the NeoLynx™ program. NeoLynx combined and averaged the individual MRM transition intensities across the flow injection profile and subsequently corrected for background signal by subtracting the average intensity prior to sample infusion. The resulting peak heights of the measured compounds were exported for further calculations in MS Excel (Microsoft).

REFERENCES

1. Pierre, G., K. Setchell, J. Blyth, M. A. Preece, A. Chakrapani, and P. McKiernan. 2008. Prospective treatment of cerebrotendinous xanthomatosis with cholic acid therapy. *J. Inherit. Metab. Dis.* 31.
2. Verrips, A., L. H. Hoefsloot, G. C. Steenbergen, J. P. Theelen, R. A. Wevers, F. J. Gabreëls, B. G. van Engelen, and L. P. van den Heuvel. 2000. Clinical and molecular genetic characteristics of patients with cerebrotendinous xanthomatosis. *Brain.* 123: 908-19.
3. Inoue, K., S. Kubota, and Y. Seyama. 1999. Cholestanol induces apoptosis of cerebellar neuronal cells. *Biochem. Biophys. Res. Commun.* 256: 198-203.
4. Seyama, Y. 2003. Cholestanol metabolism, molecular pathology, and nutritional implications. *J. Med. Food.* 6: 217-24.
5. Salen, G., T. W. Meriwether, and G. Nicolau. 1975. Chenodeoxycholic acid inhibits increased cholesterol and cholestanol synthesis in patients with cerebrotendinous Xanthomatosis. *Biochem. Med.* 14: 57-74.
6. Berginer, V. M., G. Salen, and S. Shefer. 1984. Long-Term Treatment of Cerebrotendinous Xanthomatosis with Chenodeoxycholic Acid. *N. Engl. J. Med.* 311: 1649-1652.
7. Berginer, V. M., B. Gross, K. Morad, N. Kfir, S. Morkos, S. Aaref, and T. C. Falik-Zaccai. 2009. Chronic Diarrhea and Juvenile Cataracts: Think Cerebrotendinous Xanthomatosis and Treat. *Pediatrics.* 123: 143-147.
8. van Heijst, A. F., A. Verrips, R. A. Wevers, J. R. Cruysberg, W. O. Renier, and J. J. Tolboom. 1998. Treatment and follow-up of children with cerebrotendinous xanthomatosis. *Eur. J. Pediatr.* 157: 313-6.
9. Yahalom, G., R. Tsabari, N. Molshatzki, L. Ephraty, H. Cohen, and S. Hassin-Baer. 2013. Neurological outcome in cerebrotendinous xanthomatosis treated with chenodeoxycholic acid: early versus late diagnosis. *Clin. Neuropharmacol.* 36: 78-83.
10. Huidekoper, H. H., F. M. Vaz, A. Verrips, and A. M. Bosch. 2016. Hepatotoxicity due to chenodeoxycholic acid supplementation in an infant with cerebrotendinous xanthomatosis: implications for treatment. *Eur. J. Pediatr.* 175: 143-6.
11. Appadurai, V., A. DeBarber, P.-W. Chiang, S. B. Patel, R. D. Steiner, C. Tyler, and P. E. Bonnen. 2015. Apparent underdiagnosis of Cerebrotendinous Xanthomatosis revealed by analysis of ~60,000 human exomes. *Mol. Genet. Metab.* 116: 298-304.
12. Lorincz, M. T., S. Rainier, D. Thomas, and J. K. Fink. 2005. Cerebrotendinous Xanthomatosis. *Arch. Neurol.* 62: 1459.
13. Bleyle, L., H. H. Huidekoper, F. M. Vaz, R. Singh, R. D. Steiner, and A. E. Debarber. 2016. Update on newborn dried bloodspot testing for cerebrotendinous xanthomatosis: An available high-throughput liquid-chromatography tandem mass spectrometry method. *Mol. Genet. Metab. Reports.* 7: 11-15.
14. Debarber, A. E., J. Luo, M. Star-Weinstock, S. Purkayastha, M. T. Geraghty, J. P.-W. Chiang, L. S. Merkens, A. S. Pappu, and R. D. Steiner. 2014. A blood test for cerebrotendinous xanthomatosis with potential for disease detection in newborns. *J. Lipid Res.* 55: 146-154.
15. Batta, A. K., G. Salen, S. Shefer, G. S. Tint, and M. Batta. 1987. Increased plasma bile alcohol glucuronides in patients with cerebrotendinous xanthomatosis: effect of chenodeoxycholic acid. *J. Lipid Res.* 28: 1006-1012.
16. Ferdinandusse, S., and S. M. Houten. 2006. Peroxisomes and bile acid biosynthesis. Biochim. *Biophys. Acta.* 1763: 1427-40.
17. Nakagawa, M., M. Une, S. Takenaka, Y. Tazawa, S. Nozaki, T. Imanaka, and T. Kuramoto. 2001. Urinary bile alcohol profiles in healthy and cholestatic children. *Clin. Chim. Acta.* 314: 101-6.
18. Mills, K. A., I. Mushtaq, A. W. Johnson, P. D. Whitfield, and P. T. Clayton. 1998. A method for the quantitation of conjugated bile acids in dried blood spots using electrospray ionization-mass spectrometry. *Pediatr. Res.* 43: 361-8.
19. Dayal, B., Salen, G., Padia, J., Shefer, S., Tint, G. S., Sasso, G., & Williams, T. H. (1993). Bile alcohol glucuronides: regioselective O-glucuronidation of 5β-cholestane-3α,7α,12α,25-tetrol and 24-nor-5β-cholestane-3α,7α,12α,25-tetrol. Carbohydrate Research, 240(C), 133-142. doi.org/10.1016/0008-6215(93) 84178-9

TABLE 1

DBS and CTX patient information

| DBS | Patient[a] | DBS age (y) | Storage conditions | Patient age at sampling (y) | Plasma cholestanol (mg/dl) | Plasma cholestanol (μM) | Diagnosis[b] | Phenotype at diagnosis |
|---|---|---|---|---|---|---|---|---|
| 1 | P1 | 0.5 | −20° C. | 9 | 1.62 | 42 | G/B | unknown |
| 2 | P2 | 0.5 | −20° C. | 12 | 2.57 | 66 | G/B | unknown |
| 3 | P3 | 4 | −20° C. | 17 | 1.84 | 47 | B | neonatal jaundice, intractable diarrhea, xanthomas |
| 4 | P4 | 9 | −20° C. | 16 | 3.23 | 83 | G/B | juvenile cataracts, developmental delay, autistiform behavior, cognitive impairment |
| 5 | P5 | 4 | −20° C. | 31 | 1.65 | 42 | G/B | xanthomas, spastic gait, paraparesis |
| 6 | P6 | 0.17 | −20° C. | 45 | 3.44 | 88 | B | cognitive decline, psychiatric disorder, dementia |
| 7 | P7 | 0.17 | −20° C. | 46 | 4.79 | 123 | B | depression, paraparesis, cerebellar ataxia, dystonia |
| 8 | P8 | 7.5 | −20° C. | 36 | 4.52 | 116 | G/B | cataract, xanthomas, seizures, intractable diarrhea |
| 9 | P9 | 0.5 | 4° C. | 6.2 | 1.52 | 39 | G | speech delay, altered stool pattern |
| 10 | P10 | 0.1 | 4° C. | 9 | 2.06 | 53 | B | cataracts |
| 11 | P11 | 0.5 | 4° C. | 11 | 4.52 | 116 | G | cataracts, developmental delay, autistiform behaviour, altered stool pattern |
| 12 | P12 | 6 | −20° C. | 56 | 0.84 | 22 | G/B | cataracts, xanthomas |
| 13 | NB1 | 16 | Unknown, last 8 years stored at −20° C. | 0.01 | — | — | G/B | juvenile cataracts, xanthomas, intractable diarrhea |
| 14 | NB2 | 4 | 4° C. | 0.01 | 0.86 | 22 | G | none, see (10) |

[a]NB: original neonatal screening DBS
[b]G: genetic, B: biochemical

TABLE 2

Transitions, cone voltages and collision energies for measured compounds

| Compound | MRM (m/z) | Cone voltage (V) | Collision energy (eV) |
|---|---|---|---|
| t-CDCA | 498→80 | 90 | 60 |
| [2]H$_4$-t-CDCA | 502→80 | 90 | 60 |
| t-CA | 514→80 | 90 | 60 |
| [2]H$_4$-t-CA | 518→80 | 90 | 60 |
| t-THCA | 556→80 | 90 | 60 |
| g-CDCA | 448→74 | 60 | 40 |
| [2]H$_4$-g-CDCA | 452→74 | 60 | 40 |
| g-CA | 464→74 | 60 | 40 |
| [2]H$_4$-g-CA | 468→74 | 60 | 40 |
| Pregnanediol glucuronide | 495→75 | 45 | 35 |
| Cholestane tetrol glucuronide | 611→75 | 80 | 48 |

TABLE 2(A)

Table of individual tetrol/t-CDCA and t-THCA/tetrol ratios CTX patients and ranges for controls (term/preterm) and Zellweger patients.

| DBS | Patient | Tetrol/t-CDCA | t-THCA/tetrol |
|---|---|---|---|
| 1 | P1 | 5 | 0.028 |
| 2 | P2 | 12 | 0.035 |
| 3 | P3 | 233 | 0.004 |
| 4 | P4 | 702 | 0.003 |
| 5 | P5 | 328 | 0.001 |
| 6 | P6 | 866 | 0.005 |
| 7 | P7 | 101 | 0.001 |
| 8 | P8 | 94 | 0.002 |
| 9 | P9 | 0.8 | 0.048 |
| 10 | P10 | 18 | 0.018 |
| 11 | P11 | 21 | 0.026 |
| 12 | P12 | 25 | 0.023 |
| 13 | NB1 | 22 | 0.047 |
| 14 | NB2 | 138 | 0.004 |
| Term | (range) | 0.000-0.057 | 0.19-250 |
| Preterm | (range) | 0.000-0.061 | 0.09-377 |
| Zellweger | (range) | 0.023-0.101 | 10.5-38.0 |

TABLE 3

Overview of selected (exact) masses of bile acids, bile alcohols and bile acid intermediates

| Nominal mass | Exact mass | Compound name |
|---|---|---|
| 375 | 375.2905 | 3β-hydroxy-5-cholanoic acid (litocholic acid) |
| 389 | 389.2697 | dihydroxy-cholenoic acid |
| 391 | 391.2885 | dihydroxy-cholanoic acids (e.g. chenodeoxycholic acid) |
| 405 | 405.2646 | trihydroxy-cholenoic acids, 3β,7α,12α-trihydroxy-5-cholenoic acid |
| 407 | 407.2803 | trihydroxy-cholanoic acids (e.g. cholic acid) |
| 431 | 431.3169 | 3β,7α-dihydroxy-cholestenoic acid |
| 432 | 432.3119 | 3β-hydroxy-5-cholanoic acid (litocholic acid) glycine |
| 433 | 433.3323 | dihydroxy-cholestanoic acid (e.g. DHCA) |
| 444 | 444.2755 | 7α-hydroxy-3-oxo-4-cholenoic acid glycine |
| 446 | 446.2912 | 3β,7α-dihydroxy-5-cholenoic acid glycine |
| 447 | 447.3116 | 3β,7α,12α-trihydroxy-cholestenoic acid |
| 448 | 448.3069 | dihydroxy-cholanoic acids (e.g. chenodeoxycholic acid, deoxycholic acid) glycine |
| 449 | 449.3273 | trihydroxy-cholestanoic acid (e.g. THCA) |
| 453 | 453.2316 | 3β-hydroxy-5-cholenoic acid sulfate |
| 460 | 460.2705 | 7α,12α-dihydroxy-3-oxo-4-cholenoic acid glycine |
| 462 | 462.2861 | 3β,7α,12α-trihydroxy-5-cholenoic acid glycine |
| 464 | 464.3018 | trihydroxy-cholanoic acids glycine (e.g. cholic acid) |
| 465 | 465.3222 | tetrahydroxy-cholestanoic acid (e.g. OH-THCA, varanic acid) |
| 465 | 465.3044 | cholesterol sulfate |
| 469 | 469.2265 | 3β,7α-dihydroxy-5-cholenoic acid sulfate |
| 471 | 471.2422 | dihydroxy-cholanoic acid sulfate |
| 472 | 472.3432 | 3β-hydroxy-5-cholestanoic acid glycine |
| 480 | 480.2789 | 3β-hydroxy-5-cholanoic acid taurine |
| 480 | 480.2967 | tetrahydroxy-cholanoic acids glycine |
| 482 | 482.2946 | 3β-hydroxy-5-cholanoic acid (litocholic acid) taurine |
| 485 | 485.2215 | 3β,7α,12α-trihydroxy-5-cholenoic acid sulfate |
| 487 | 487.2371 | trihydroxy-cholanoic acid sulfate |
| 488 | 488.3381 | 3β,7α-dihydroxy-cholestenoic acid glycine |
| 490 | 490.3538 | dihydroxy-cholestanoic acid (e.g. DHCA) glycine |
| 494 | 494.2582 | 7α-hydroxy-3-oxo-4-cholenoic acid taurine |
| 498 | 498.2895 | dihydroxy-cholanoic acids (chenodeoxycholic acid) taurine |
| 506 | 506.3487 | dihydroxy-cholestanoic acid (e.g. THCA) glycine |
| 507 | 507.3327 | $C_{29}$-dicarboxylic acid |
| 510 | 510.2531 | 7α,12α-dihydroxy-3-oxo-4-cholenoic acid taurine |
| 510 | 510.2531 | 3β-hydroxy-5-cholenoic acid glycine and sulfate |
| 514 | 514.2844 | trihydroxy-cholanoic acids (cholic acid) taurine |
| 522 | 522.3259 | 3β-hydroxy-5-cholestanoic acid taurine |
| 526 | 526.2480 | 3β,7α-dihydroxy-5-cholenoic acid glycine and sulfate |
| 528 | 528.2637 | dihydroxy-cholanoic acids (e.g. chenodeoxycholic acid) glycine and sulfate |
| 530 | 530.2793 | tetrahydroxy-cholanoic acids taurine |
| 540 | 540.3364 | dihydroxy-cholestanoic acid (e.g. DHCA) taurine |
| 542 | 542.2429 | 3β,7α,12α-trihydroxy-5-cholenoic acid glycine and sulfate |
| 552 | 552.3000 | 7α,12α-dihydroxy-3-oxo-4-cholestenoic acid taurine |
| 554 | 554.3157 | trihydroxy-cholestenoic acid (e.g. THCA:1) taurine |
| 556 | 556.3313 | trihydroxy-cholestanoic acid (e.g. THCA) taurine |
| 567 | 567.3175 | dihydroxy-cholanoic acids glucuronide |
| 570 | 570.3106 | tetrahydroxy-cholestenoic acids (e.g. OH-THCA:1) taurine |
| 572 | 572.3263 | tetrahydroxy-cholestanoic acids (e.g. OH-THCA) taurine |
| 583 | 583.3124 | trihydroxy-cholanoic acids glucuronide |
| 586 | 586.3055 | pentahydroxy-cholestenoic acids (e.g. diOH-THCA:1) taurine |
| 588 | 588.3212 | pentahydroxycholestanoic acid taurine |
| 609 | 609.3644 | 5β-cholestanetriol-?-one glucuronide, 5β-cholestenetetrol glucuronide |
| 611 | 611.3801 | 5β-cholestenetetrol glucuronide |
| 611 | 611.3437 | tetrahydroxy-27-nor-5β-cholestane-24-one glucuronide |
| 613 | 613.3593 | 27-nor-5β-cholestanepentol glucuronide |
| 625 | 625.3593 | tetrahydroxy-5β-cholestane-?-one glucuronide, 5β-cholestenepentol glucuronide |
| 627 | 627.3750 | 5β-cholestanepentol glucuronide |
| 627 | 627.3386 | pentahydroxy-27-nor-5β-cholestane-24-one glucuronide |
| 629 | 629.3543 | 27-nor-5β-cholestanehexol glucuronide |
| 641 | 641.3543 | 5β-cholestanepentol-?-one glucuronide, 5β-cholestenehexol glucuronide |
| 643 | 643.3699 | 5β-cholestanehexol glucuronide |
| 643 | 643.3335 | hexahydroxy-27-nor-5β-cholestane-24-one glucuronide |
| 645 | 645.3492 | 27-nor-5β-cholestaneheptol glucuronide |
| 651 | 651.3862 | dihydroxy-cholanoic acid glycine and N-acetylglucosamine |
| 659 | 659.3648 | 5β-cholestancheptol glucuronide |
| 701 | 701.3689 | dihydroxy-cholanoic acid taurine and N-acetylglucosamine |

Example 2

Figure 6:
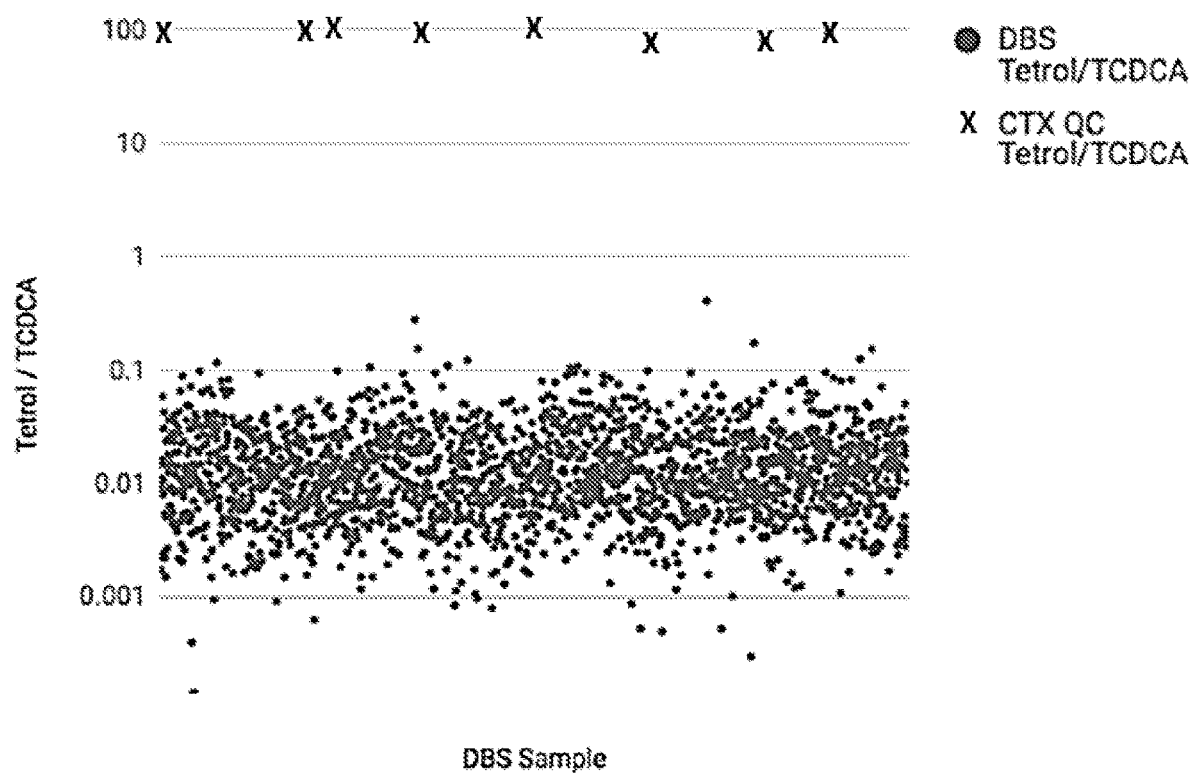
FIG. 6 shows 10.000 blood spots screened by UPLC-MS/MS assay. Note the logarithmic scale for Tetrol/TCDCA, the low results for the screened blood spots (•) and the positive control, from a confirmed CTX patient (X).

Using UPLC MS/MS, tetrol/T-CDCA and T-THCA/tetrol ratios were determined in approximately 10.000 blood spots of neonates. No positives and thus no false positives were observed. Cut off level was based on 5 confirmed CTX patients. Results are shown in FIG. 6.

Example 3

We performed a pilot with the flow-injection MS analysis which is also used for routine newborn screening. The official newborn screening laboratory in the Academisch Medisch Centrum performed the routine extraction of ⅛ inch punches using the currently used Neobase II kit on blood spots of 10 CTX patients (including 2 original newborn screening samples), 3 Zellweger patients and 200 controls (150 term and 50 preterm babies) (see Table below). Analysis of the extract was done in the Laboratory of Genetic Metabolic Diseases on a 11-year old Premier-XE mass spectrometer (Waters) that is technically less advanced compared the currently used mass spectrometers in modern newborn screening laboratories. This means that the current setup for neonatal screening will certainly be able to use this method. For our analysis we used routine flow-injection analysis and used Neolynx software to calculate the abundances of T-THCA (m/z 556.2), tetrol glucuronide (m/z 611.3) and T-CDCA (m/z 498.2) followed by the calculation of the ratio's. The results are very clear, the tetrol/T-CDCA and the T-THCA/tetrol ratio's clearly identify the CTX patients without overlap with the controls (term and preterm). Combining the two ratio's makes the identification of the CTX samples unambiguous and possible false positives (Zellweger patients can have elevated tetrol glucuronide) are avoided.

| Sample | T-THCA/tetrol | Tetrol/T-CDCA |
| --- | --- | --- |
| Original CTX neonatal screening card | 0.001 | 1919.00 |
| Original CTX neonatal screening card | 0.001 | 121.45 |
| CTX | 0.003 | 351.00 |
| CTX | 0.003 | 332.00 |
| CTX | 0.003 | 63.00 |
| CTX | 0.003 | 62.40 |
| CTX | 0.004 | 264.00 |
| CTX | 0.005 | 2.92 |
| CTX | 0.007 | 2.31 |
| CTX | 0.032 | 3.00 |
| Zellweger 1 | 4.5 | 0.33 |
| Zellweger 2 | 15.3 | 0.09 |
| Zellweger 3 | 17.2 | 0.08 |
| Term (N = 150) | 0.059-134 | 0-1.0 |
| Preterm (N = 50) | 0.080-124 | 0-0.21 |

The invention claimed is:

1. A method of identifying 27-hydroxylase (CYP27A1) deficiency in an animal, the method comprising:
   receiving a dried blood spot comprising a blood sample from said animal;
   enriching the blood sample by liquid chromatography, protein precipitation, liquid-liquid extraction, solid-liquid extraction, or ultrafiltration;
   detecting, by mass analysis of the enriched blood sample, an intensity signal of at least a bile alcohol glucuronide and a C27- or C24-bile acid or a conjugate thereof, wherein the C27- or C24-bile acid or conjugate thereof is selected from the group consisting of:
   cholic acid (CA), tauro-cholic acid (t-CA); glyco-cholic acid (g-CA); chenodeoxycholic acid (CDCA); tauro-chenodeoxycholic acid (t-CDCA); glyco-chenodeoxycholic acid (g-CDCA);
   trihydroxycholestanoic acid (THCA); tauro-trihydroxycholestanoic acid (t-THCA); glyco-trihydroxycholestanoic acid (g-THCA); dihydroxycholestanoic acid (DHCA); tauro-dihydroxycholestanoic acid (t-DHCA); and glyco-dihydroxycholestanoic acid (g-DHCA);
   calculating a ratio between the intensity signals of said bile alcohol glucuronide and said C24- or C27-bile acid or conjugate thereof;
   comparing said ratio between the intensity signals of said bile alcohol glucuronide and said C24- or C27-bile acid or conjugate thereof with a ratio of a control sample or control value from a control animal of the same species as the animal but without CYP27A1 deficiency; and
   identifying the animal as having hydroxylase (CYP27A1) deficiency, based on said comparison of said ratios.

2. The method according to claim 1, wherein said bile alcohol glucuronide is cholestanetetrol glucuronide (tetrol).

3. The method according to claim 1, wherein the intensity signal is determined of a stable isotope labeled compound selected from the group consisting of: bile alcohol glucuronide, a C24- or C27-bile acid, or a conjugate thereof, and wherein said intensity signal of said stable isotope labeled compound is compared to the intensity of said at least a bile alcohol glucuronide and a C24- or C27-bile acid or conjugate thereof.

4. The method according to claim 1, wherein at least the intensity signal is determined of a C24-bile acid or conjugate thereof and of a C27-bile acid or conjugate thereof, wherein said C24-bile acid or conjugate thereof is selected from the group consisting of:
   cholic acid (CA), tauro-cholic acid (t-CA), glyco-cholic acid (g-CA), chenodeoxycholic acid (CDCA), tauro-chenodeoxycholic acid (t-CDCA), and glyco-chenodeoxycholic acid (g-CDCA),
   and said C27-bile acid or conjugate thereof is selected from the group consisting of:
   trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA).

5. The method according to claim 1, wherein said mass analysis is selected from the group consisting of: mass spectrometry (MS), High-resolution MS, liquid chromatography—mass spectrometry (LC-MS), matrix-assisted laser desorption/ionization—time of flight mass spectrometry (MALDI-TOF), quadrupole time of flight mass spectrometry (Q-TOF), Orbitrap-MS, and flow-injection MS.

6. The method according to claim 1, wherein said animal is a human.

7. The method according to claim 1, wherein said animal is a newborn.

8. The method according to claim 1, further comprising measuring the intensity signal of said bile alcohol glucuronide or C24- or C27-bile acid or a conjugate thereof, relative to the intensity signal of an isotopically labeled standard.

9. The method according to claim 8, wherein said isotopically labeled standard comprises a stable isotope labeled C24- or C27-bile acid or a conjugate thereof selected from the group consisting of:
   cholic acid (CA), tauro-cholic acid (t-CA), glyco-cholic acid (g-CA), chenodeoxycholic acid (CDCA), tauro-chenodeoxycholic acid (t-CDCA), glyco-chenodeoxycholic acid (g-CDCA), trihydroxycholestanoic acid (THCA), tauro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA).

10. The method of claim 9, wherein said method comprises a step of ionizing the biological sample using a cone voltage of about 60 to about 90 V.

11. A kit comprising a stable isotope labeled C24- or C27-bile acid or a conjugate thereof selected from the group consisting of:

cholic acid (CA), tauro-cholic acid (t-CA), glyco-cholic acid (g-CA), chenodeoxycholic acid (CDCA), tauro-chenodeoxycholic acid (t-CDCA), glyco-chenodeoxycholic acid (g-CDCA), trihydroxycholestanoic acid (THCA), tau ro-trihydroxycholestanoic acid (t-THCA), glyco-trihydroxycholestanoic acid (g-THCA), dihydroxycholestanoic acid (DHCA), tauro-dihydroxycholestanoic acid (t-DHCA), and glyco-dihydroxycholestanoic acid (g-DHCA); and further comprising a positive control sample, wherein the positive control sample is a dried blood spot comprising a blood sample from a control animal of the same species as the animal but with cerebrotendinous xanthomatosis (CTX).

* * * * *